United States Patent [19]

Nappholz et al.

[11] Patent Number: 4,702,253
[45] Date of Patent: Oct. 27, 1987

[54] METABOLIC-DEMAND PACEMAKER AND METHOD OF USING THE SAME TO DETERMINE MINUTE VOLUME

[75] Inventors: Tibor A. Nappholz, Englewood; Mark Lubin; Harry L. Valenta, Jr., both of Aurora, both of Colo.

[73] Assignee: Telectronics N.V., Curacao, Netherlands Antilles

[21] Appl. No.: 787,125

[22] Filed: Oct. 15, 1985

[51] Int. Cl.⁴ .............................................. A61N 1/36
[52] U.S. Cl. .............................................. 128/419 PG
[58] Field of Search ............... 128/419 PG, 721–725, 128/716, 734

[56] References Cited

U.S. PATENT DOCUMENTS

| | | | |
|---|---|---|---|
| 3,593,718 | 7/1971 | Krasner et al. | 128/419 PG |
| 4,535,774 | 8/1985 | Olson | 128/419 PG |
| 4,567,892 | 2/1986 | Plicchi et al. | 128/419 PG |
| 4,576,183 | 3/1986 | Plicchi et al. | 128/419 PG |
| 4,596,251 | 6/1986 | Plicchi et al. | 128/725 |

OTHER PUBLICATIONS

Hamilton et al, "Ventilation Monitor Based on Transthoracic Impedance Changes", *Med Res Eng*, vol. 11, No. 3, May–Jun. 1972, pp. 20–24.

*Primary Examiner*—William E. Kamm
*Attorney, Agent, or Firm*—Gottlieb, Rackman & Reisman

[57] ABSTRACT

A metabolic-demand pacemaker in which the standby rate is a function of minute volume. Electrodes are placed in a blood vessel in the vicinity of the patient's pleural cavity, a known current field is established in the blood, and the impedance in the field is measured. The impedance is a function of the pleural pressure which, in turn, is a function of the patient's minute volume. The system also includes a mechanism for calibrating the standby rate to equal the nominal standby rate for a minute volume which equals a long-term average value, with the standby rate being changed in accordance with the deviation of the minute volume from the long-term average value.

28 Claims, 7 Drawing Figures

METABOLIC-DEMAND PACEMAKER AND METHOD OF USING THE SAME TO DETERMINE MINUTE VOLUME

DESCRIPTION

This invention relates to pacemakers, and more particularly to metabolic-demand pacemakers and methods of using the same to determine a patient's minute volume.

The term "demand" in the pacemaker art generally denotes a pacemaker which stimulates the heart only when there is a need for stimulation. Typically, in a VVI pacemaker, the timer which controls the generation of a stimulating pulse is reset when an R wave is sensed, thus ensuring that a stimulus is generated only when there is a demand for it. The term "metabolic-demand" as used to characterize a pacemaker has a completely different meaning. It refers to the rate at which the pacemaker paces the heart, in the absence of spontaneous beating, as being dependent upon the true metabolic demand of the human body.

The concept of providing a metabolic-demand pacemaker is very old. One of the earliest approaches involved monitoring the respiration rate of the patient; the faster the breathing, the greater the need for oxygen to be transported in the blood throughout the body, and the faster the required pacing rate. In the past few years, a number of other methods have been proposed for making the pacing rate reflect the true metabolic demand. In addition to respiration rate, the QT interval, body sounds, oxygen saturation and blood temperature have all been used as measurable parameters for controlling the pacing rate. The prior art methods were not satisfactory, however, because either the relationships of the measured parameters to true metabolic demand were not well defined, or there were problems with sensor stability or complexity.

It has been suggested by others that a satisfactory parameter would be minute volume. The minute volume is a measure of the average amount of air being breathed by the patient; the greater the minute volume, the faster should the heart beat. The relationship results from the fact that both minute volume and heart rate are controlled by the nervous system, and the same body parameters influence both. Minute volume is known from extensive medical investigation to be an excellent indicator of metabolic demand. All physical activity consumes oxygen, and oxygen consumption is directly related to the replenishing process, i.e., minute volume. Measuring the respiration rate alone is insufficient to indicate physical activity because a patient may increase his air intake not only through rate, but also through volume change. [The term "minute volume" would appear to refer to the volume of air breathed in during the course of a minute. The term as used herein is broader, however, in that it does not contemplate measurements which necessarily extend for exactly one minute. It is simple enough, for example, to determine the volume breathed in during the course of one minute from a measurement taken over only thirty seconds. The term minute volume as used herein refers to the average amount of air breathed in by the patient, while the actual measurement interval may extend from several seconds all the way to longer than a minute.]

Minute volume is a function of two factors—the volume of air breathed in during each breath, and the rate at which the patient is breathing. Adding up the individual breaths for a certain period of time provides a measure of the minute volume. In general, doing this for too short an interval, e.g., a few seconds, can give rise to inaccurate results. The reason for this is that considerably different results will be obtained if the measurement interval starts just before a breath or just after it. On the other hand, performing the measurement over too long an interval is also inadvisable because the response of the pacemaker will be too slow. In general, a measurement interval of 20-30 seconds is preferred, although intervals outside this range are also possible. The real problem, however, is how to measure the amount of air breathed in by the patient. Prior art techniques for measuring minute volume have not been satisfactory. Generally, a transducer is placed across the rib cage of the patient, with the movement of the ribs reflecting the expansion of the lungs. This measurement technique suffers from the disadvantages of poor resolution and susceptibility to motion artifacts, and is not sufficiently reliable to find use in a pacemaker.

Our invention is based upon the realization that the volume of air in the lungs is related to a corresponding pressure called pleural pressure. The pleural pressure, in the pleural cavity, manifests itself in a change in the diameter of blood vessels in the immediate vicinity of the cavity. The blood in the vessels comprises a volume conductor, and its impedance is measured by establishing a known current field and measuring the voltage which develops in the field. The impedance change which is due to respiration depends on the particular placement of the current source electrodes as well as the voltage sense electrodes. Preferably, the current source is established between the blood in the right ventricle and the pacemaker case, and the voltage is measured between either the high right atrium or the superior vena cava ("SVC") and the pacemaker case. If there is no pacing catheter in the right ventricle, then the current may be established between the blood in the atrium and the pacemaker case. However, the preferred blood vessel for use is the SVC, one of the two large veins which return blood to the heart. The SVC is also the vein along which all transvenous electrodes for pacemakers pass to get to the right ventricle, and that is why the SVC is the ideal blood vessel for use in practicing our invention. The modulation in the impedance measurement is a direct measure of the minute volume. By monitoring the degree of the impedance change during the course of each breath, the volume of air contained in the breath (called the "tidal volume") can be determined. Simply by summing these values over a fixed period of time, a measure of minute volume can be obtained.

While the basic operating principle of our invention is easy to understand, there are other factors to consider. Consider a minute volume measurement taken over a 20-second interval. If there is a doubling during a measurement interval, it is not desirable to suddenly change the pacing rate of the heart by a correspondingly significant amount. [Minute ventilation can vary by a factor of about 4-14 depending upon the patient, while the heart rate varies by about a factor of 2, depending upon the patient. Although it is possible to construct a pacemaker which would allow the function of minute volume versus rate to be programmed, in the illustrative embodiment of the invention the pacing rate doubles for a minute volume which increases by a factor of 8. Thus a doubling of the minute volume does not result in a doubling of the rate but the change, if abrupt, can still be undesirable.]

One of the most severe problems is that there is no permanent relationship between the measured minute volume and the pacing rate. A typical pacemaker is programmed to have a particular standby rate, the minimum rate at which the heart should be paced. Theoretically, there is a minimum minute volume, associated with minimal physical activity, which corresponds with this programmed standby rate. As the patient exercises, the minute volume increases and, in accordance with the principles of our invention, so will the standby rate. It is found over long periods of time, however, that the minute volume measurement does not return to the original value. This is not to say that the real minute volume for minimal physical activity has changed, but rather that the measurement value has changed. This can be due to many factors, such as a change in electrode position or even the conductivity of the blood. There must be some way to accommodate for long-term changes in the minute volume measurement, that is, changes which can properly be attributed to permanent or semi-permanent factors, as opposed to instantaneous metabolic demand.

In accordance with the principles of our invention, the minute volume is averaged over a long period of time in order to determine an average value. This long-term average value is assumed to be the minimum minute volume and to correspond with the programmed standby rate. An instantaneous minute volume (measured over the 20-second measurement interval) less than the long-term average does not affect the pacing rate; the programmed (minimum) standby rate is used. It is only when the instantaneous value exceeds the average value that it is assumed that there is a short-term need for more oxygen, and the standby rate is adjusted accordingly. The instantaneous rate can be increased or decreased, to a degree dependent upon the amount by which the instantaneous minute volume exceeds the long-term average. The long-term average can increase or decrease, with the long-term average at any time corresponding with the programmed standby rate.

It is in this way that the system adapts itself to permanent and even long-term changes. Another way of looking at it is that the pacing rate is calibrated to equal the nominal (or programmed standby) rate for a minute volume which equals the long-term average value, with the instantaneous rate being changed in accordance with the deviation of the minute volume from the long-term average value.

The basic objective of our invention thus is to provide novel and improved metabolic-demand pacemakers and methods of using the same to determine a patient's minute volume.

Further objects, features and advantages of our invention will become apparent upon consideration of the following detailed description thereof when read in conjunction with the hereto annexed drawing, in which:

Figure 1:
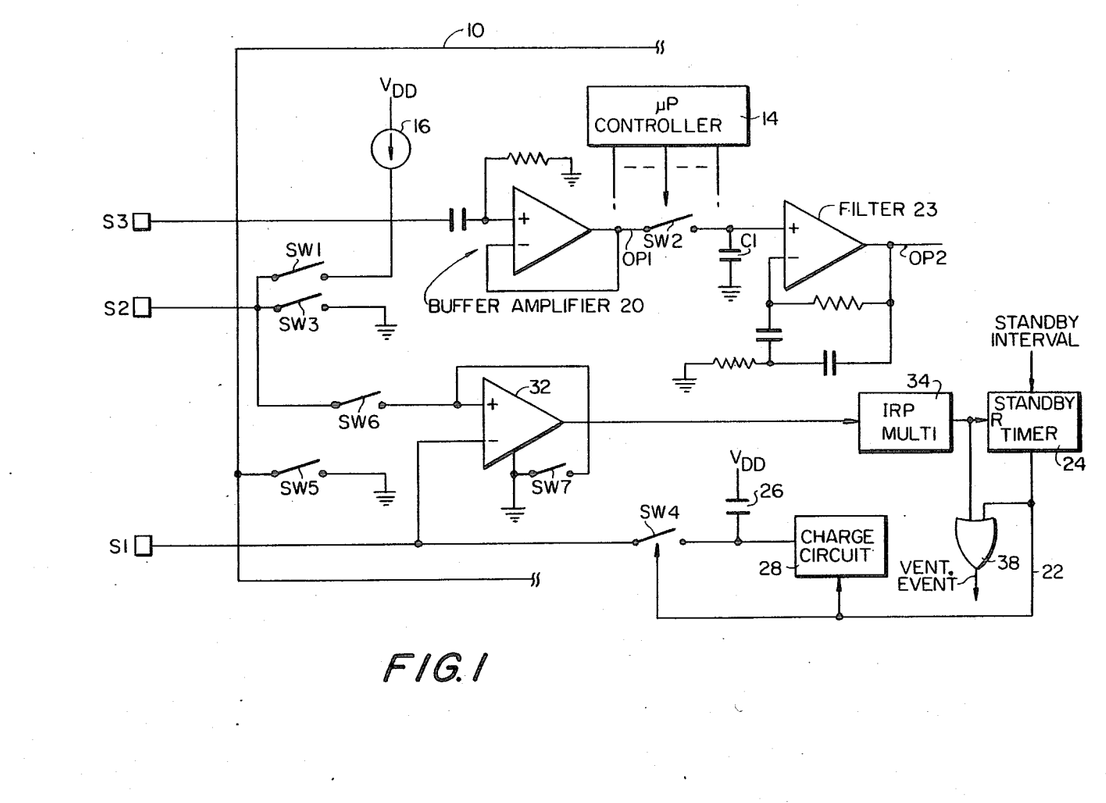
FIG. 1 depicts the input/output section of a pacemaker constructed in accordance with the principles of our invention.
Figure 2:
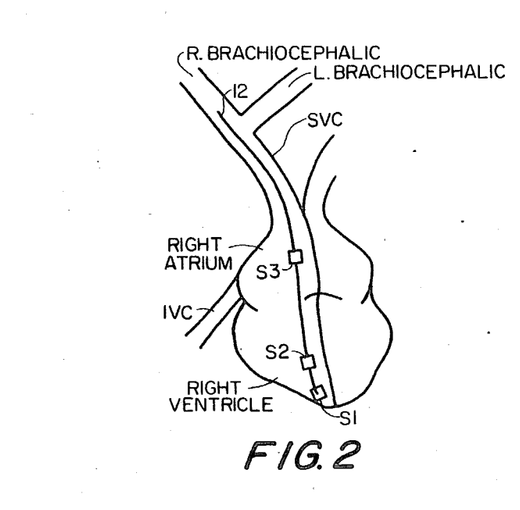
FIGS. 2, 2A and 2B depict a human heart and three possible approximate placements of electrodes.

As shown in FIG. 1, the pacemaker includes a case 10 and three electrodes S1, S2 and S3. The electrodes are shown in FIG. 2 all disposed along a single catheter 12 which is extended through the SVC to the patient's heart. Electrode S1 is the conventional pacing/sensing electrode. The indifferent electrode in the illustrative embodiment of the invention is the case itself, as will be described. Electrode S2 is used for current sourcing, i.e., to apply a current which flows in the blood between the electrode and the pacemaker case, and electrode S3 is used to measure the respiratory impedance between the electrode and the case.

Figure 2A:
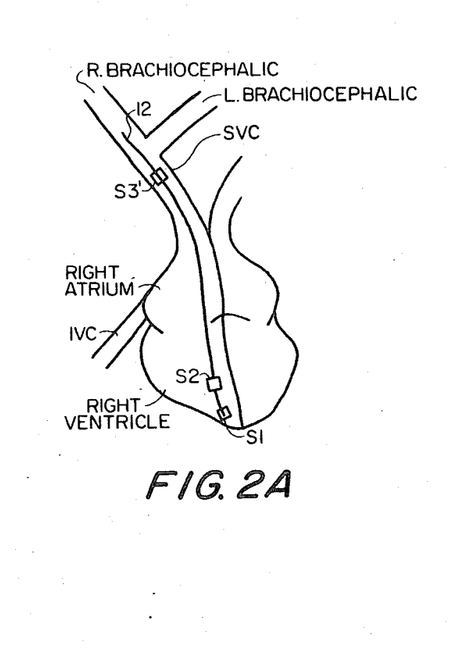
Figure 2B:
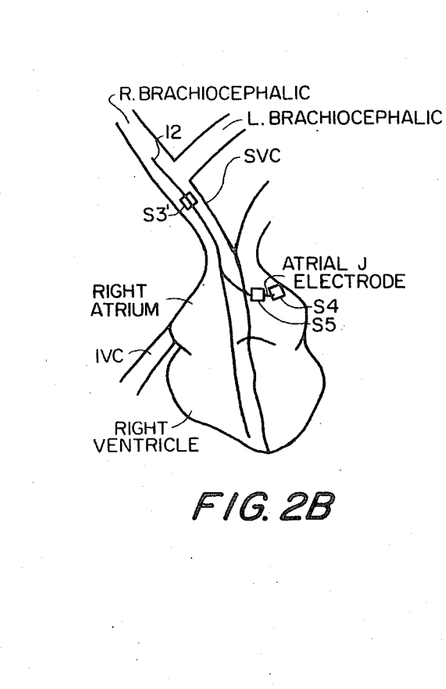

Alternative electrode placements are also shown in FIGS. 2A and 2B. In the arrangement of FIG. 2A, the impedance measurement electrode (which is designated S3 in FIG. 1) may be placed, for example, in the SVC and is designated S3'; in general, the electrode used for the impedance measurement may range in position from the vicinity of the high right atrium to 3–4 cm above the margin. In the arrangement of FIG. 2B, in the absence of a ventricular pacing catheter, but where a conventional atrial J electrode S4 is provided, an electrode S5 may be used for current sourcing and an additional electrode such as S3' may be used for sensing. All of electrodes S2, S3 and S5 are conventional ring electrodes. In general, the sensitivity and the signal/noise ratio are compromised if the current sourcing is done in the endocardium rather than in the blood. The case is used for both current sourcing and impedance measurement not only to save electrodes, but also because it has been found to provide an improved signal/noise ratio. When the pacemaker also requires atrial pacing or sensing, and utilizes a conventional atrial J electrode, as shown in FIG. 2B, the positioning of electrode S3' is relatively simple because the distance between the SVC-atrial margin and the atrial appendage is relatively well defined. Thus when an atrial electrode is used, the rings which comprise electrodes S5 and S3' may be fixed relative to the atrial electrode, thereby simplifying their proper positioning in the SVC. When only a ventricular electrode is used, as in FIG. 2A, the distance between the SVC-atrial margin and the ventricular apex is typically 10–18 cms. In this case, it will usually be necessary, after placing the ventricular electrode, to fix the position of electrode S3 by changing the curvature of the electrode portion within the heart.

Figure 3:
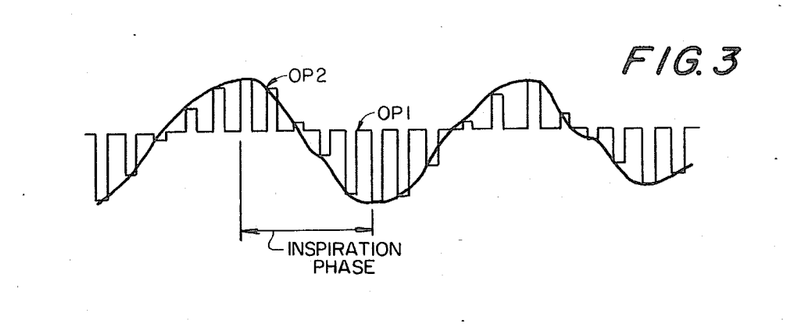
FIG. 3 depicts the signals which appear on the conductors labelled OP1 and OP2 of FIG. 1.

All switches are under the control of microprocessor controller 14. One output of the controller is shown extended to switch SW2, but it is to be understood that the switches SW1, SW3, SW5, SW6 and SW7 are similarly controlled. With switches SW1 and SW5 closed, and switch SW3 open, current from constant-current source 16 flows from electrode S2 through the blood to grounded case 10. Depending upon the blood impedance, the voltage at electrode S3 relative to the case changes. This voltage is extended through the buffer amplifier 20 and switch SW2 (which follows the state of switch SW1), and sampled on capacitor C1 at the input of filter 23. The waveform of the input to the filter, OP1, is shown in FIG. 3. Typically, the switches SW1, SW2 and SW5 are closed for 20-60 microseconds, 100 times per second. The resistors and capacitors associated with filter 23 pass frequencies between about 0.05 Hz and 1.0 Hz, the standard range for respiration rate measurements. The waveform of the output of the filter, OP2, is also shown in FIG. 3. It is apparent that the OP2 signal is the envelope, suitably filtered, free of the faster transients contained in OP1. (The waveforms of FIG. 3 are not drawn to scale.)

During a measurement interval, switches SW4 and SW6 are open, and switch SW7 is closed; pace and sense functions are briefly disabled. Although sensing is disabled while the impedance measurement is being performed, even 60 microseconds is so short an interval relative to heart signals that disabling the sensing during this time is of no importance.

Unipolar pacing is used in the illustrative embodiment of the invention. In order to pace the heart, switches SW4 and SW5 are closed. Switch SW5 connects the case to the circuit ground, so that the case serves as the indifferent electrode during the pacing. Switch SW4 is closed by a signal extended over control lead 22 by standby timer 24. The standby timer is a conventional timer (whose function, like many of those depicted by circuit blocks, can be controlled by a microprocessor) for controlling a pacing pulse when a spontaneous beat has not been sensed for an interval equal to the standby interval. The standby interval itself is derived from the circuit of FIG. 5, as will be described, and is extended to the timer. The pacer includes a standard storage capacitor 26 and charge circuit 28 for furnishing the pacing pulse when needed. During pacing, the state of switch SW3 is not important. Switches SW1 and SW2 should be open since impedance measurements should not be performed during pacing. The states of switches SW6 and SW7 are not critical, although preferably the former is held open and the latter is held closed.

The pacemaker shown in the drawing is capable of unipolar sensing or bipolar sensing; element 32 is an amplifier-filter commonly used for heart signal detection. The status switch SW7 determines the sensing mode, and switch SW7 can be a programmable parameter. (The programming circuit is not shown. For example, referring to FIG. 5, it will be seen that there is a register 30 which contains a standby rate. While it is fixed in the illustrative embodiment of the invention, it is to be understood that it can be a programmable parameter as is known in the art.) In the unipolar mode, switch SW7 is closed. The plus input of difference amplifier 32 is thus connected to circuit ground, and the minus input is connected to electrode S1. Switch SW5 is closed to connect the case to circuit ground. Switches SW1 and SW2 are, of course, held open since they are closed only in order to conduct an impedance measurement. Switch SW5 should be closed so that the case is grounded. Switch SW6 is held open, and unipolar sensing proceeds with the plus input of amplifier 32 grounded through switch SW7. The state of switch SW3 is not important.

When the system is operated in the bipolar sensing mode, switch SW7 is open. Switch SW6 is closed during the sensing, so that electrode S2 is connected to the plus input of difference amplifier 32. Electrode S1 is still connected to the minus input, so that the voltage which is sensed is that which appears across electrodes S1 and S2. Switch SW3 must be open in this case so as not to short electrode S2 to the case. The case should be grounded through switch SW5.

Although switch SW5 is always closed, as described, the switch is shown should bipolar pacing be employed. In that case the switch should be opened during pacing.

The remaining circuitry in FIG. 1 is straightforward. The output of sense amplifier 32 triggers an IRP (interference reversion period) multivibrator 34. This multivibrator causes sensed signals which are too close to each other to be ignored. The output of the multivibrator resets standby timer 24 to start a new ventricular-ventricular timing interval. The interval itself is determined by the output of the standby in-use latch 36 in FIG. 5. This element will be described below. Whenever the timer times out, switch SW4 is closed and a pacing pulse is generated. An OR gate 38 is used to signal the occurrence of a ventricular event. The two inputs to the OR gate are the output of the timer 24, representing the generation of a pacing pulse, and the output of the IRP multivibrator 34, representing a spontaneous beat. The output of the OR gate is extended to the clock input of latch 36 in FIG. 5, the purpose of which will be described below.

It should be noted that four electrodes have been used in the past to perform an impedance measurement to determine the volume of blood in the right ventricle. (This has nothing to do with providing a measurement of minute volume.) Only two electrodes are used to measure blood impedance in the illustrative embodiment of the invention. The current source electrode is preferably made with a larger surface area and the surface is prepared with platinum black or sintering to increase the effective area. The voltage sense electrode is ideally a small platinum electrode.

With reference to FIG. 3, it will be seen that the inspiration phase corresponds to a decreasing blood impedance. It is during the inspiration phase that the pleural pressure is decreased, which is why the lungs fill up with air in the first place and increase in volume. A decrease in pressure results in decompression of the veins and a decrease in the impedance measurement.

It is the peak-to-peak transition in the OP2 signal of FIG. 3 which is directly proportional to the tidal volume, that is, the amount of air inhaled in one breath. If successive peak-to-peak measurements are summed, the sum will represent the total amount of air breathed in during the measurement interval. It is the circuit of FIG. 4 which both determines the peak-to-peak values, and also adds them all up during a 20-second measurement interval.

Figure 4:
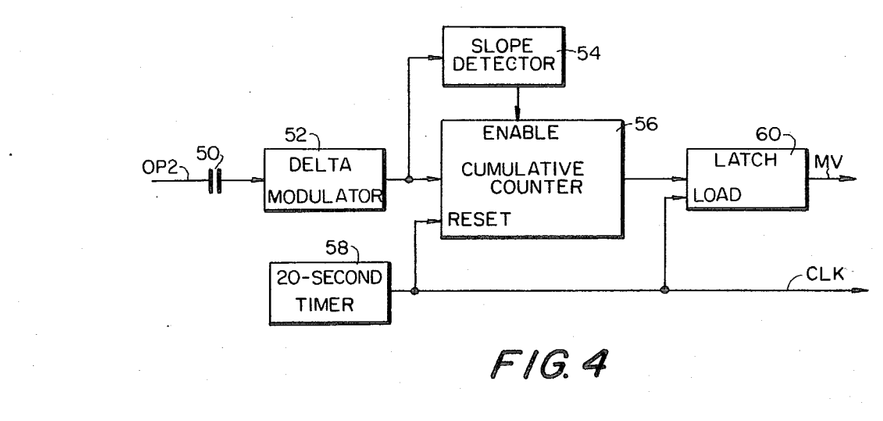
FIG. 4 is the processing section of the illustrative embodiment of our invention, having an input OP2 connected to the OP2 output of FIG. 1, and two outputs MV and CLK.

A preferred way to process a physiological signal is to use a delta modulator. Delta modulator processing is in and of itself a standard technique. Reference may be had, for example, to Pat. Nos. 4,466,440, 4,448,196 and 4,509,529. The OP2 signal is coupled through capacitor 50 to delta modulator 52. The output of the delta modulator is a series of 1 and 0 bit values, as is known in the art. The bit stream is extended to the input of slope detector 54. The output of the slope detector is energized whenever the slope of the OP2 signal is negative. Slope detectors per se are also well known in the art. (A typical strategy, for example, is to determine the slope by monitoring whether 0's or 1's predominate over a predetermined number of bits.) Cumulative counter 56 is enabled whenever the slope of the OP2 signal is negative. For each bit at the output of the delta modulator, the counter increments or decrements its count, depending upon the polarity of the bit. Thus during the inspiration phase, the count will increase (assuming that bits of value 1 correspond to decreases in the OP2 signal) by an amount equal to the difference between the number of 1's and the number of 0's. This, in turn, is a function of the peak-to-peak magnitude of the OP2 signal. Because the counter is enabled during every negative sloping portion of the OP2 signal, the cumulative count is a measure of the sum of the peak-to-peak values. The counter is reset at 20-second intervals under control of timer 58, and thus the output of counter 56 at the end of every measurement interval is directly proportional to the average minute volume over the preceding 20 seconds. (This is considered to be an "instantaneous" value.) At the end of every measurement interval, the load input of latch 60 is pulsed and the final count is loaded in the latch. The counter then resets so that another measurement may be taken. Thus the multi-bit value on cable MV represents the instantaneous minute volume, and a pulse on the CLK conductor is an indication that a new value has been derived. These two signals are used by the circuit of FIG. 5. This is the circuit which not only determines the standby rate in accordance with the instantaneous minute volume, but also calibrates the nominal standby rate to the long-term, or average, value of minute volume.

Figure 5:
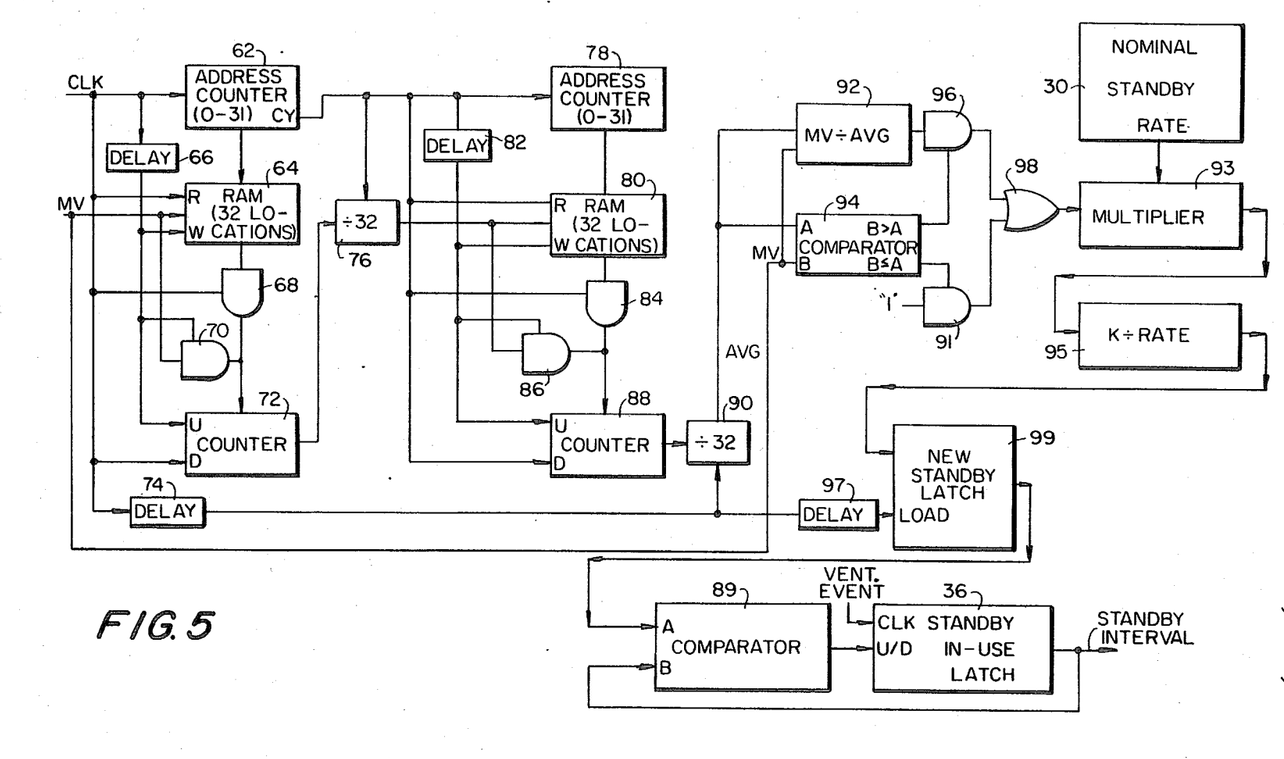
FIG. 5 is the third stage of the illustrative embodiment of our invention, having two inputs, CLK and MV, connected to the outputs of the circuit of FIG. 4, a VENT. EVENT input connected to a corresponding output in the circuit of FIG. 1, and a STANDBY INTERVAL output connected to a corresponding input in the circuit of FIG. 1.

The circuit of FIG. 5 includes a random-access memory 64 which contains 32 locations. Address counter 62 contains five stages so that its count cycles between 0 and 31. Each CLK pulse advances the counter. Following a count of 31, the next CLK pulse causes the counter to be reset to zero and a carry pulse to be extended to address counter 78. This counter is similar to counter 62, with the carry outputs of counter 62 serving as the clock input. It is thus apparent that counter 62 cycles 32 times for each cycling of counter 78. RAM 80 is similar to RAM 64. The address bits of counter 62 identify a storage location in memory 64, while the address bits of counter 78 select a storage location in memory 80.

Memory 64 is used to store the 32 most recent minute volume samples, that is, the samples taken over the last 10 minutes and 40 seconds. These 32 values are used to form an average. The actual average is computed by adding together the most recent 32 samples, and then dividing by 32. Each time a new sample is derived, the oldest sample is discarded, and the newest sample takes its place. It is in this way that the average reflects the most recent samples. The running sum is contained in counter 72. This counter can count up or down, depending upon whether its up or down count input is energized at the same time that a sample is applied by gate 68 to its data input. (Gate 68 and many of the other individual gates in FIG. 5 really represent multiple gates for transmitting bits in parallel. For the sake of drawing simplicity, no distinction is made between single-bit and multi-bit operations. In each case, when it is a multi-bit value which is transmitted, it will be apparent that a group of gates must be used even though only one is shown.)

With the arrival of each CLK pulse, address counter 62 advances, and thus identifies the oldest sample in memory 64. The CLK pulse is applied to the read input of the memory, and it also enables gate 68. Consequently, the oldest sample stored in the memory is transmitted through the gate to the input of counter 72. The CLK pulse is also applied to the down count input of the counter, and thus the oldest sample is subtracted from the running count maintained by the counter. Delay unit 66 delays the CLK pulse slightly. The delayed pulse is applied to the write input of the memory. The latest minute volume sample is applied to the data input of the memory, and thus this sample gets stored in the memory. The same sample is extended through gate 70, which gate is also energized by the delayed CLK pulse, for application to the data input of counter 72. Because the delayed CLK pulse now energizes the up count input of the counter, the latest sample is added to the running count. It is in this manner that the oldest sample is subtracted from the running count and the latest sample is added to it, in order to update the average. The newest sample also replaces the oldest sample in the memory so that 32 sample times from now, the system will know the value of the oldest sample which should be subtracted from the running count.

As described above, the most recent minute volume sample is always compared with a long-term average in order to determine how the standby rate should be controlled. In the preferred embodiment, the long-term average which is used is taken over a much longer period of time than 10 minutes and 40 seconds, the time interval during which the 32 most recent samples were taken. In order to form an average over a much longer period of time, the second memory 80 is used. What is done is to take the 32 samples stored in memory 64 and to average them. This is accomplished simply by taking the count in counter 72 and dividing it by 32. The average value is then stored in memory 80. The two memory circuits function in an almost identical fashion, the only difference being that what is stored in memory 80 each time is an average value taken over 32 sample times.

At the end of each complete cycling of address counter 62, after 32 new samples have been stored in memory 64 following the last complete cycling of the address counter, a carry pulse is generated. This pulse serves to trigger divider 76, which divides the count in counter 72 by 32. Thus the data value at the output of the divider is comparable to the MV input to the circuit of FIG. 5. The difference is that while the MV input represents the latest minute volume sample, the output of the divider represents the average value over the last 32 samples. The carry output from address counter 62 also serves as a clock pulse, and is analogous to the CLK input. The carry pulse cycles address counter 78 so that a new location in memory 80 is identified. The carry pulse energizes the read input of the memory as well as gate 84, so that the oldest average value stored in the memory is transmitted through the gate to the data input of counter 88. Because the carry output of address counter 62 energizes the down count input of counter 88, the oldest average value is subtracted from the running count. After a delay introduced by element 82, the newest average value is extended through gate 86 to the data input of the counter. At the same time, the up count input of the counter is energized so that the newest average value is added to the count. Also, because the write input of the memory is energized, the newest average value is stored in memory 80.

Delay unit 74 serves to delay each incoming clock pulse slightly in order to allow the count maintained by counter 88 to be up-dated should address counter 62 have completed a cycle. The pulse at the output of delay unit 74 energizes divide-by-32 element 90 so that what appears on the AVG output of the divider is an average value taken over the last 32×32 samples.

It should be appreciated that there is a delay between the long-term average value at the output of divider 90 and the current sample. Counter 88 is up-dated only at intervals of 10 minutes and 40 seconds, and thus the long-term average value is not even influenced by the most current samples. This is of no moment, however. The only reason for maintaining a long-term average value is to calibrate the system by establishing a correspondence between the programmed standby rate maintained in register 30 and the long-term minute volume average value. The current minute volume value is compared with the long-term value, and there is no reason to be concerned about updating the long-term value rapidly.

The current value is applied to the B input of comparator 94, and the long-term average value is applied to the A input of the comparator. The comparator energizes one of its two outputs, as indicated. Should the current value be less than or equal to the long-term average value, then gate 91 is enabled. A data value is transmitted through this gate and OR gate 98 to the input of multiplier 93; this data value is unity. The data input to multiplier 93 is the programmed standby rate stored in register 30, and in this case the output of the multiplier is simply the programmed, or nominal, standby rate.

On the other hand, if the current value is greater than the long-term average value, gate 96 is energized. The MV and AVG inputs are applied to divider 92, which divider forms the ratio shown. The ratio will be greater than unity only if the current value is greater than the average value, and it is only at this time that gate 96 is operated. Thus the upper input of OR gate 98 causes a value to be transmitted to multiplier 93 only if the value is greater than unity. The net result is that the input to multiplier 93 is equal to the ratio of the current minute volume value to the long-term average value, but the ratio never drops below unity.

The reason for this is that the output of multiplier 93 represents the desired standby rate. The desired rate can never be less than the programmed rate. Consequently, the input to the multiplier from OR gate 98 can never be less than unity. The output of the multiplier can only be equal to or greater than the programmed rate, depending upon the degree by which the current minute volume exceeds the long-term average.

The multiplier does not simply multiply its two inputs to derive an output. As mentioned above, minute volume for a typical patient can vary between limits which differ by as little as a factor of 4 or as much as a factor of 14. It would hardly be desirable to increase the standby rate by even 4 times because this would certainly cause the patient to be paced at too fast a rate. In the illustrative embodiment of the invention, the multiplier operates linearly, and it is designed to double the standby rate when the minute volume increases by a factor of 8. This means that the multiplier has a straight-line transfer characteristic which passes through two points on a standby rate versus MV/AVG plot. One point has a standby rate equal to the nominal value and an MV/AVG ratio of unity, and the other has a standby rate which is twice the nominal rate and an MV/AVG value of 8.

It should be borne in mind that the reason for deriving a long-term average value is in order to accommodate the system to long-term variations which may arise due to changes in body chemistry, re-positioning of electrodes, etc., that is, factors which would otherwise cause a permanent change in the standby rate even when there is no cause for it. Consider for example a long-term minute volume average value measurement which slowly increases not because of changes in metabolic demand, but rather because of electrode re-positioning. Whatever the initial value, suppose that the current minute volume is greater than the long-term average. The MV/AVG ratio is thus greater than unity, and the standby rate exceeds the nominal value. As the minute volume changes from sample time to sample time (over intervals of 20 seconds), the standby rate changes as well. But the standby rate can never drop below the nominal value because the output of multiplier 93 never drops below the nominal value. As the long-term average value increases, the instantaneous standby rate output of the multiplier is still a function of the difference between the current rate and the long-term value. Over the long term, should the patient not be exercising and should there be no need for a rate above the nominal value, as the long-term value increases eventually the current value will equal the long-term value, assuming that the increase in measurement value is not due to changes in metabolic demand or the true minute volume, but rather is due to the measurement system itself. It does not matter if the minute volume measurement value increases because the MV/AVG ratio will be unity and the nominal standby rate will apply.

On the other hand, suppose that for one reason or another the measurement value starts to decrease, not due to metabolic demand, but rather to a change in system performance. In this case the MV/AVG ratio will be less than unity and the standby rate will apply. It is only when the long-term average value catches up to the current value that the ratio will be unity. As long as the current value is less than the average value, the nominal standby rate applies. Even slight increases in the current value, as long as they do not exceed the average value, will not result in an increase in the standby rate from the nominal value. It is only after the average value drops sufficiently that fluctuations in the current value which exceed it will cause an increase in the standby rate. Thus the patient's heart is paced at a controlled rate in accordance with the patient's minute volume, but the system includes means for calibrating that controlled rate to be equal to the nominal standby rate for a minute volume which equals the long-term average value; the controlled rate is changed in accordance with the deviation of the minute volume from the long-term average value.

The output of multiplier 93 represents the new, or desired, standby rate. The input to standby timer 24 of FIG. 1, however, is a standby interval, that is, a value which represents time. In order to convert rate to time, divider 95 is provided. It simply forms the inverse of the desired rate and multiplies it by an appropriate scale factor K so that the new standby interval at the output of divider 95 is in terms of units to which timer 24 of FIG. 1 is calibrated.

The output of element 95, however, is not extended directly to the input of timer 24. The reason for this is that a new minute volume sample is derived only every 20 seconds. Were the standby interval which corresponds to the new minute volume value to change immediately, the rate at which the patient's heart is paced might change every 20 seconds. Abrupt changes are not desirable. For this reason, the rate at which the pacing rate is allowed to change is limited.

The output of divider 95 is applied to the data input of latch 99. This latch contains the new (desired) standby rate. The pulse at the output of delay element 74 is applied to delay element 97, and the latter element pulses the load input of latch 99 by the time a new value appears at the data input. The new standby value, updated every 20 seconds, is applied to the A input of comparator 89. Latch 36 contains the standby value which is in current use, the standby interval at the latch output being extended to timer 24 in FIG. 1. The standby interval in use is also connected to the B input of comparator 89. Consequently, the output of comparator 89 is high or low, depending upon whether the new standby interval is greater or less than the interval currently in use.

The output of the comparator is extended to the up/-down count input of latch 36. The clock input of the latch is pulsed each time that the heart beats. Referring to FIG. 1, it will be recalled that the output of OR gate 38 goes high whenever an R wave is sensed, or whenever a stimulus is generated. Each time that latch 36 is clocked, the standby interval stored in it is incremented or decremented, depending upon the direction in which the value must change in order to equal the new value. Thus if the new value is greater than the value in use, for example, the value in use will be incremented on each ventricular event. The net result is that the rate at which the standby rate is allowed to change is limited. It is allowed to change only in fixed increments or decrements, and only whenever there is ventricular activity. (A most convenient time to change the standby rate is when a ventricular event occurs; the new standby interval begins with a heartbeat. However, it is certainly conceivable that the standby interval would be allowed to change at a controlled rate which is independent of heart activity and is a function of time only.)

Although the invention has been described with reference to a particular embodiment, it is to be understood that this embodiment is merely illustrative of the application of the principles of the invention. For example, the measuring circuit could include four poles, with the extreme poles—which could encompass the right side of the heart and the SVC—furnishing the current and the inner poles measuring the voltage gradients. Thus it is to be understood that numerous modifications may be made in the illustrative embodiment of the invention and other arrangements may be devised without departing from the spirit and scope of the invention.

We claim:

1. A metabolic-demand pacemaker comprising means for pacing a patient's heart at a controlled rate, means for placement in a blood vessel in the vicinity of the patient's pleural cavity and for monitoring the impedance of the blood therein, the blood impedance varying in accordance with the patient's pleural pressure, means responsive to said monitoring means for determining the patient's minute volume, and means for changing said controlled rate in accordance with the patient's minute volume.

2. A metabolic-demand pacemaker in accordance with claim 1 wherein said determining means includes means for summing successive peak blood impedance changes for a predetermined time interval.

3. A metabolic-demand pacemaker in accordance with claim 2 further including means for representing a nominal standby rate, means responsive to said determining means for calculating a long-term minute volume average value, and means for calibrating said controlled rate to equal said nominal standby rate for a minute volume which equals the long-term average value, and wherein said changing means includes means for changing said controlled rate in accordance with the deviation of the minute volume from the long-term average value.

4. A metabolic-demand pacemaker in accordance with claim 3 further including means for limiting the rate at which said controlled rate is allowed to change.

5. A metabolic-demand pacemaker in accordance with claim 4 wherein said pacemaker includes a case and said monitoring means includes first and second electrodes for placement in said blood vessel, means for causing a fixed current to flow through the blood in said vessel between said first electrode and the pacemaker case, and means for measuring the voltage across said second electrode and the pacemaker case to monitor the impedance of said blood.

6. A metabolic-demand pacemaker in accordance with claim 5 wherein a catheter is used to couple the pacemaker to the patient's heart, and said first and second electrodes are fixed in position along said catheter.

7. A metabolic-demand pacemaker in accordance with claim 4 wherein said pacemaker includes a case, said pacing means includes a first electrode, and said monitoring means includes second and third electrodes for placement in said blood vessel, means for causing a fixed current to flow through the blood in said vessel between said second electrode and the pacemaker case, and means for measuring the voltage across said third electrode and the case to monitor the impedance of said blood.

8. A metabolic-demand pacemaker in accordance with claim 7 wherein a catheter is used to couple the pacemaker to the patient's heart, and said first, second and third electrodes are fixed in position along said catheter.

9. A metabolic-demand pacemaker in accordance with claim 1 further including means for representing a nominal standby rate, means responsive to said determining means for calculating a long-term minute volume average value, and means for calibrating said controlled rate to equal said nominal standby rate for a minute volume which equals the long-term average value, and wherein said changing means changes said controlled rate in accordance with the deviation of the minute volume from the long-term average value.

10. A metabolic-demand pacemaker in accordance with claim 9 wherein said pacemaker includes a case and said monitoring means includes first and second electrodes for placement in said blood vessel, means for causing a fixed current to flow through the blood in said vessel between said first electrode and the pacemaker case, and means for measuring the voltage across said second electrode and the pacemaker case to monitor the impedance of said blood.

11. A metabolic-demand pacemaker in accordance with claim 9 wherein said pacemaker includes a case, said pacing means includes a first electrode, and said monitoring means includes second and third electrodes for placement in said blood vessel, means for causing a fixed current to flow through the blood in said vessel between said second electrode and the pacemaker case, and means for measuring the voltage across said third electrode and the case to monitor the impedance of said blood.

12. A metabolic-demand pacemaker in accordance with claim 1 wherein said pacemaker includes a case and said monitoring means includes first and second electrodes for placement in said blood vessel, means for causing a fixed current to flow through the blood in said vessel between said first electrode and the pacemaker case, and means for measuring the voltage across said second electrode and the pacemaker case to monitor the impedance of said blood.

13. A metabolic-demand pacemaker in accordance with claim 12 wherein a catheter is used to couple the pacemaker to the patient's heart, and said first and second electrodes are fixed in position along said catheter.

14. A metabolic-demand pacemaker in accordance with claim 1 wherein said pacemaker includes a case, said pacing means includes a first electrode, and said monitoring means includes second and third electrodes for placement in said blood vessel, means for causing a fixed current to flow through the blood in said vessel between said second electrode and the pacemaker case, and means for measuring the voltage across said third electrode and the case to monitor the impedance of said blood.

15. A metabolic-demand pacemaker in accordance with claim 14 wherein a catheter is used to couple the pacemaker to the patient's heart, and said first, second and third electrodes are fixed in position along said catheter.

16. A metabolic-demand pacemaker in accordance with claim 1 further including means responsive to said determining means for calculating a long-term minute volume average value, and wherein said changing means includes means for changing said controlled rate in accordance with the deviation of the minute volume from the long-term average value.

17. A metabolic-demand pacemaker in accordance with claim 16 wherein said monitoring means includes a pair of electrodes for placement in said blood vessel, and means coupled to said electrodes for causing a fixed current to flow through the blood in said vessel and for measuring the voltage across said blood to determine the impedance of said blood.

18. A metabolic-demand pacemaker in accordance with claim 17 wherein a catheter is used to couple the pacemaker to the patient's heart, and said electrodes are fixed in position along said catheter.

19. A metabolic-demand pacemaker in accordance with claim 1 further including means for limiting the rate at which said controlled rate is allowed to change.

20. A metabolic-demand pacemaker in accordance with claim 19 further including means for representing a nominal standby rate, means responsive to said determining means for calculating a long-term minute volume average value, and means for calibrating said controlled rate to equal said nominal standby rate for a minute volume which equals the long-term average value, and wherein said changing means includes means for changing said controlled rate in accordance with the deviation of the minute volume from the long-term average value.

21. A metabolic-demand pacemaker in accordance with claim 19 wherein said monitoring means includes a pair of electrodes for placement in said blood vessel, and means coupled to said electrodes for causing a fixed current to flow through the blood in said vessel and for measuring the voltage across said blood to determine the impedance of said blood.

22. A metabolic-demand pacemaker in accordance with claim 21 wherein a catheter is used to couple the pacemaker to the patient's heart, and said electrodes are fixed in position along said catheter.

23. A method of determining a patient's minute volume comprising the steps of placing electrodes in a blood vessel in the vicinity of the patient's pleural cavity, monitoring the blood impedance between predetermined points, the blood impedance varying in accordance with the patient's pleural pressure, and deriving the patient's minute volume from the variations in the monitored blood impedance.

24. A method in accordance with claim 23 wherein the patient's minute volume is derived by summing successive peak blood impedance changes for a predetermined time interval.

25. A method in accordance with claim 24 further including the step of calculating a long-term minute volume average value from the monitored blood impedance, and wherein the patient's minute volume is derived by comparing variations in the monitored blood impedance with the average value.

26. A method in accordance with claim 23 further including the step of calculating a long-term minute volume average value from the monitored blood impedance, and wherein the patient's minute volume is derived by comparing variations in the monitored blood impedance with the average value.

27. A method in accordance with claim 26 wherein said monitoring step includes the sub-steps of causing a fixed current to flow through the blood in said vessel, and measuring the voltage across two predetermined points to determine the impedance of said blood.

28. A method in accordance with claim 23 wherein said monitoring step includes the sub-steps of causing a fixed current to flow through the blood in said vessel, and measuring the voltage across two predetermined points to determine the impedance of said blood.

* * * * *

UNITED STATES PATENT AND TRADEMARK OFFICE

CERTIFICATE EXTENDING PATENT TERM
UNDER 35 U.S.C. § 156

PATENT NO.:      4,702,253

DATED:           October 27, 1987

INVENTORS:       Tibor A. Nappholz et al.

PATENT OWNER:    Telectronics N.V.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

349 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks